(12) United States Patent
Weiss

(10) Patent No.: US 6,936,053 B1
(45) Date of Patent: Aug. 30, 2005

(54) OCULAR IMPLANT NEEDLE

(76) Inventor: Jeffrey N. Weiss, 7600 Ventura La., Parkland, FL (US) 33067

(*) Notice: Subject to any disclaimer, the term of this patent is extended or adjusted under 35 U.S.C. 154(b) by 0 days.

(21) Appl. No.: 10/421,425

(22) Filed: Apr. 23, 2003

Related U.S. Application Data

(63) Continuation-in-part of application No. 10/330,914, filed on Dec. 27, 2002, which is a continuation-in-part of application No. 09/949,071, filed on Sep. 7, 2001, which is a continuation-in-part of application No. 09/109,454, filed on Jul. 2, 1998, now Pat. No. 6,402,734.

(51) Int. Cl.$^7$ ............................................... A61F 9/00
(52) U.S. Cl. ...................... 606/107; 604/264; 604/272; 604/117
(58) Field of Search ................ 604/264, 239, 604/272–274, 521, 117, 115, 97, 58–64, 104, 604/174, 97.01; 606/166–167, 170, 185, 606/4, 107, 161, 162, 6.12; 600/3, 7, 12; 623/6.12

(56) References Cited

U.S. PATENT DOCUMENTS

| | | | | |
|---|---|---|---|---|
| 4,692,142 A | * | 9/1987 | Dignam et al. | 604/521 |
| 4,735,612 A | * | 4/1988 | Chevalier | 604/130 |
| 4,760,847 A | * | 8/1988 | Vaillancourt | 606/185 |
| 4,863,428 A | * | 9/1989 | Chevalier | 604/130 |
| 5,055,107 A | * | 10/1991 | Lester | 604/540 |
| 5,078,700 A | * | 1/1992 | Lambert et al. | 604/264 |
| 5,167,645 A | * | 12/1992 | Castillo | 604/272 |
| 5,919,158 A | * | 7/1999 | Saperstein et al. | 600/500 |
| 5,964,740 A | * | 10/1999 | Ouchi | 604/264 |
| 6,258,064 B1 | * | 7/2001 | Smith et al. | 604/164.12 |
| 6,413,245 B1 | * | 7/2002 | Yaacobi et al. | 604/264 |
| 6,508,802 B1 | * | 1/2003 | Rosengart et al. | 604/523 |
| 6,551,291 B1 | * | 4/2003 | de Juan et al. | 604/294 |
| 2001/0025185 A1 | * | 9/2001 | Laufer et al. | 606/169 |
| 2003/0018299 A1 | * | 1/2003 | Stone | 604/135 |
| 2004/0044329 A1 | * | 3/2004 | Trudell | 604/507 |

\* cited by examiner

*Primary Examiner*—Cris L. Rodriguez
(74) *Attorney, Agent, or Firm*—Daniel S. Polley, P.A.

(57) ABSTRACT

An apparatus and method for safely cannulating a blood vessels, including but not limited retinal blood vessels, is described. In one embodiment, the apparatus can consist of a micropipette/microcannula, micromanipulator and positioner mounted to a base, which is attached to a wrist rest commonly used in eye surgery. The micropipette/microcannula is connected to tubing such that a medication may be injected through the micropipette/microcannula into the blood vessel or conversely, a small quantity of material may be removed from a blood vessel. Alternatively, a catheter, wire or stent may be placed through the micropipette/microcannula to treat or diagnose an area remote from the insertion site. The ability to cannulate a retinal blood vessel should be efficacious in the treatment of vein and artery occlusion, ocular tumors and other retinal, vascular and optic nerve disorders that would benefit from diagnosis and/or treatment. In another embodiment, a self-sealing needle is provided which allows the perforation of a blood vessel or other structure and the minimization of hemorrhaging when the needle is withdrawn from the blood vessel/structure. Another embodiment discloses an ocular implant needle.

17 Claims, 7 Drawing Sheets

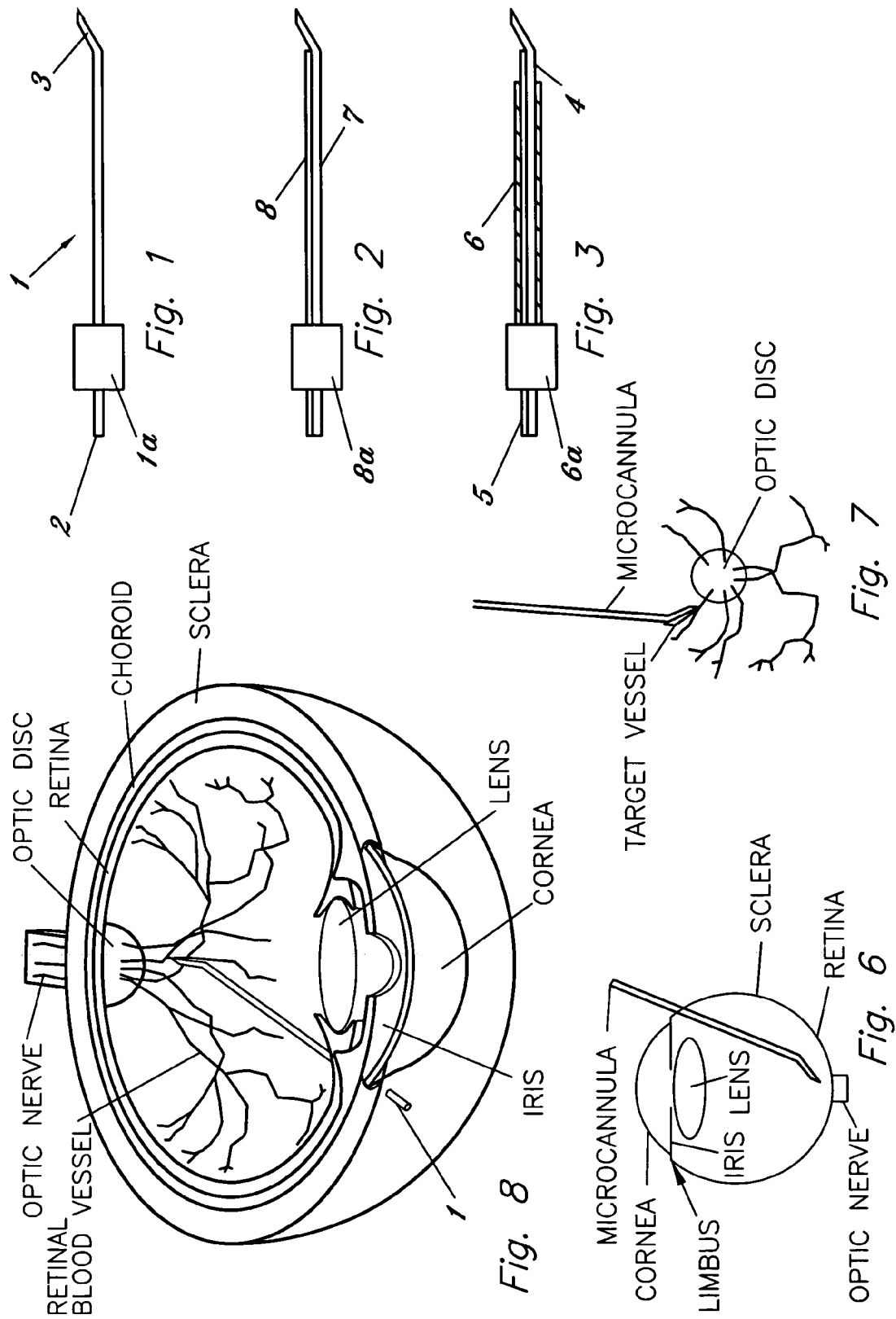

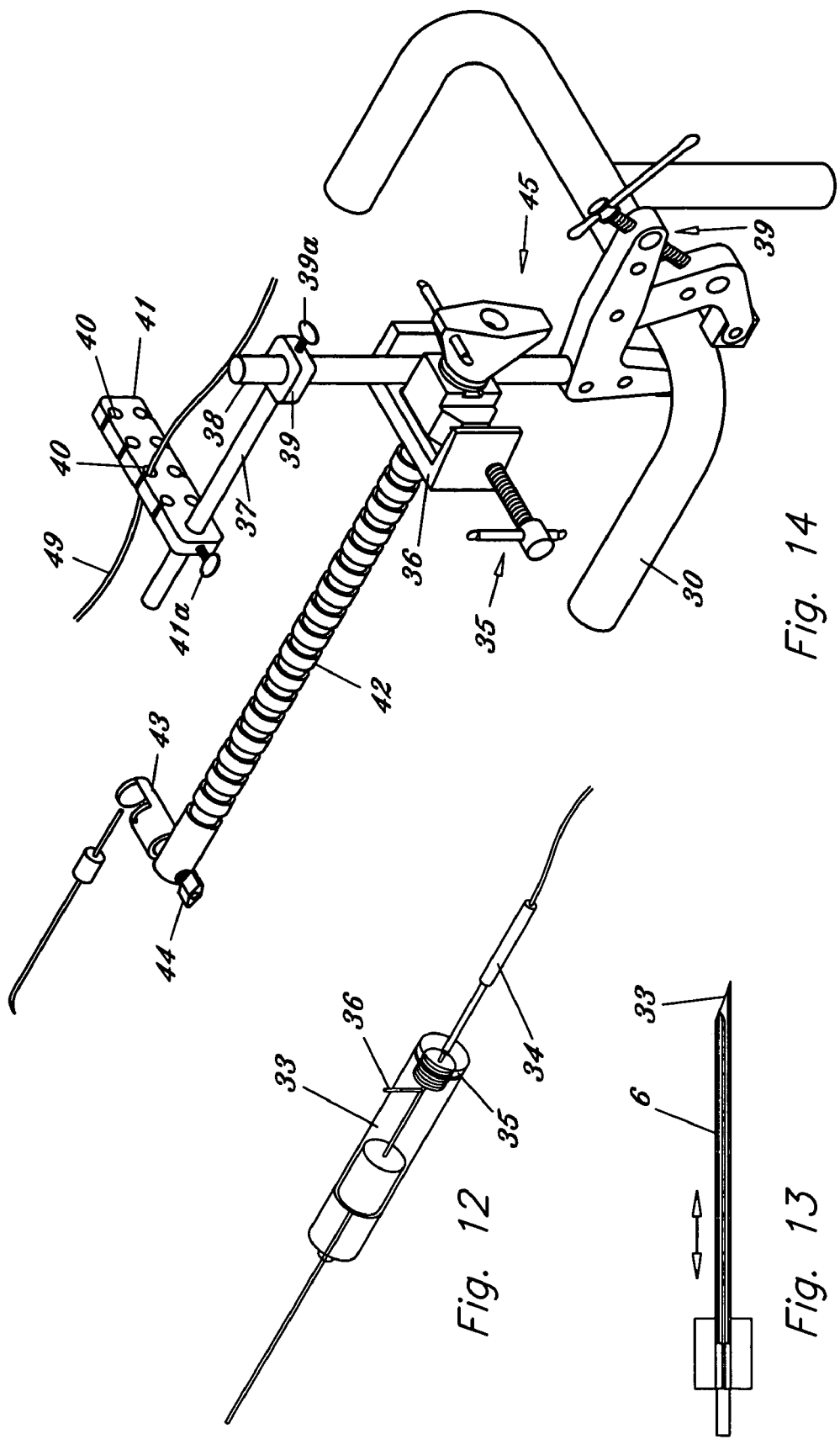

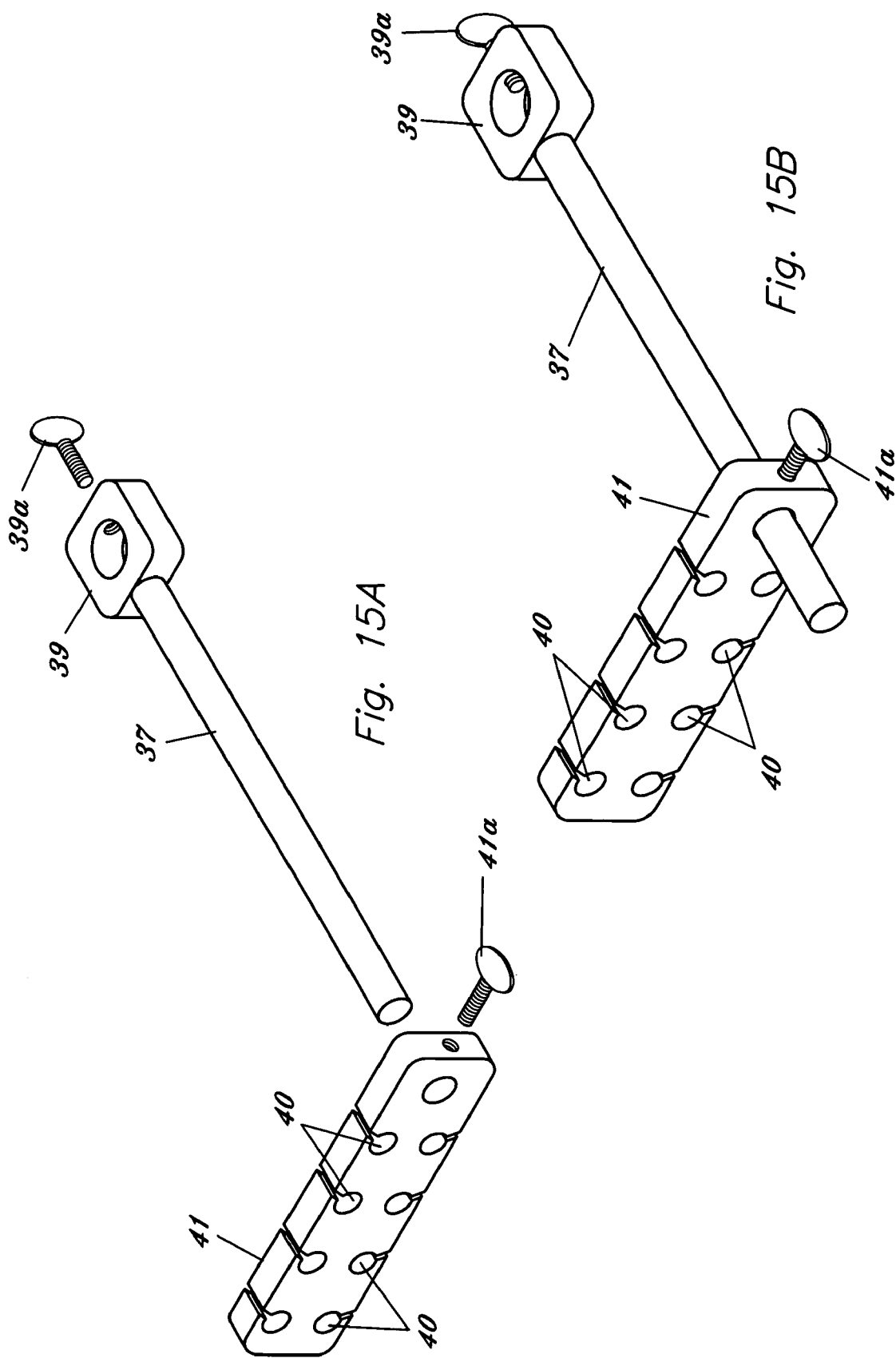

OCULAR IMPLANT NEEDLE

CROSS-REFERENCE TO RELATED APPLICATIONS

This application is a continuation-in-part of U.S. application Ser. No. 10/330,914, filed Dec. 27, 2002, which is a continuation-in-part of U.S. application Ser. No. 09/949,071, filed Sep. 7, 2001, which is a continuation-in-part of U.S. application Ser. No. 09/109,454, filed Jul. 2, 1998 now U.S. Pat. No. 6,402,734 (all of the above-identified applications are incorporated by reference). This invention was disclosed in the Disclosure Documents Program of the U.S. Patent and Trademark Office on May 4, 1998, Disclosure Document No. 435938.

BACKGROUND OF THE INVENTION

1. Field of the Invention

This invention relates to medical diagnostic and therapeutic methods and, in particular, to a method for cannulating blood vessels, including, but not limited to retinal blood vessels, such that a medication may be injected or a quantity of fluid removed from the blood vessel. Alternatively, a catheter, wire or stent may be placed through the cannula to treat or diagnose an area remote from the insertion site.

2. Description of Related Art

The cannulation of a retinal blood vessel is difficult as the lumen of the blood vessels is less than 200 microns in size. The present day ocular instruments are too large to cannulate the vessel and the dexterity required to maintain the cannula within the blood vessel for several minutes is not commonly available. The piercing of a blood vessel elsewhere in the body to inject medications, perform surgical procedures or remove blood for analysis and treatment is commonly performed. It is therefore, to the effective resolution of the aforementioned problems and shortcomings that the present invention is directed.

Furthermore, perforating a blood vessel or other structure to withdraw blood, inject or infuse a substance into the blood vessel, thread a catheter, wire, fiber or other device into a blood vessel are established procedures in medicine. It is common practice to apply pressure for a variable length of time to the perforation or cannulation site once the needle, cannula, catheter, wire, etc. is withdrawn. Generally if the perforation site is in a small blood vessel near the skin surface and/or a small gauge needle is used the application of pressure should minimize the extravasation of blood from the puncture site. However, in situations where the blood vessel or structure is large or deep to the skin surface, or a large bore needle is used, or the patient has a bleeding proclivity from a blood abnormality or uses a medication that delays blood clotting, significant hemorrhaging may occur once the device is removed from the blood vessel or structure. This may happen despite the application of pressure for a limited amount of time or despite the application of a pressure bandage.

Accordingly, it is an object of this invention to provide a microcannula or micropipette whose lumen is small enough to be safely placed within the lumen of a retinal blood vessel and by its configuration is parallel to the lumen when placed through a standard sclerotomy site, as commonly used in vitreoretinal surgery.

It is another object of this invention to provide, by its configuration and method of attachment, a stable support such that the micropipette may be securely held within the blood vessel so that subsequent maneuvers may be safely accomplished.

It is still another object of this invention to provide a micromanipulator such that the micropipette may be remotely advanced to perforate the retinal blood vessel.

It is yet another object of this invention to provide a portable device that may be easily attached to a standard operating surgical wrist rest and is stable in its "X", "Y" and "Z" planes.

It is a further object of this invention to provide a device that, by its configuration and method of attachment, does not inhibit the surgeon's view when using an operating microscope or otherwise interfere with the use of the operating microscope.

It is yet another object of this invention to provide a safe method such that the surgical procedure may be performed.

Another object of the invention is to provide a device that by the nature of its design will lessen or eliminate the amount of hemorrhage that occurs when a needle, cannula, catheter, wire, stent, fiber or other device is removed from a blood vessel or other structure.

Another object of this invention is to provide a device that can easily perforate a designated blood vessel.

Another object of this invention is to provide a device that by its nature and design is compatible with existing syringes, cannulas, catheters, etc.

Another object of this invention is to provide an ocular implant needle.

BRIEF SUMMARY OF THE INVENTION

The foregoing objects are achieved and the foregoing problems are solved in the embodiments of the invention in which a retinal blood vessel is cannulated using a micropipette (microcannula) attached to a micromanipulator which is connected to a positioner or stabilization system attached to a standard surgical wrist rest.

More particularly, a sclerotomy can be made at the standard distance from the limbus and an illuminated infusion cannula can be placed through the sclera at this point. A pars plana vitrectomy may or may not be necessary with further experience. Another sclerotomy can be made at the standard distance from the limbus such that the micropipette/microcannula is substantially parallel to the retinal blood vessel chosen to be cannulated. The micropipette is then placed through the sclerotomy overlying the selected retinal blood vessel. The intraocular pressure can be lowered to approximately 5 mm of Mercury to allow dilation of the vessel. Once the blood vessel is perforated, it may be advantageous to raise the intraocular pressure to minimize bleeding. The retinal blood vessel may be cannulated manually or the micromanipulator used to advance the micropipette into the retinal blood vessel.

The micropipette tip is preferably at an approximately 135-degree angle to the shaft such that it is parallel to the lumen of the blood vessel in the posterior retina when placed through a standard sclerotomy site. The tip of the micropipette is preferably approximately 100 microns in diameter or smaller so it may safely enter the lumen of the retinal blood vessel. The opposite end of the micropipette can be connected to and in fluid communication with a standard surgical tubing and/or syringe such that fluid may be withdrawn or injected into the retinal vessel. Alternatively, a catheter or wire may be advanced through the microcannula for diagnosing, testing or treatment of an area located at a distance from the insertion site.

In certain situations medication such as Tissue Plasminogen Activator ("t-PA") made by Genetech, Inc. and sold under the trademark ACTIVASE can be injected into the retinal vessel. Alternatively, a dye can be injected into the retinal vessel for diagnosing purposes.

The micromanipulator is preferably attached to a positioner or stabilization system that is freely mobile and stable in the "X", "Y" and "Z" directions. In the preferred embodiment, the positioner or stabilization system is securely attached to a standard ophthalmic surgery wrist rest by conventional means. The positioner or stabilization system is easy to attach to the wrist rest and may be removed when the device is not needed. At the conclusion of the maneuver, the intraocular pressure may be raised in order to minimize retinal hemorrhaging and the micropipette removed from the blood vessel. The operation is then concluded in standard fashion.

If the illumination is incorporated within the infusion line and infusion cannula then the illumination/infusion line may be placed into a illumination positioner that can be mounted on the stabilization post attached to the surgical wrist-rest. The illumination positioner may be adjustable in the x, y and z planes such that the angle of the fiber optic illumination relative to the eye may be set. This is beneficial in directing the light to the area of the retina that the surgeon is working on.

In another embodiment of the microcannula, a sheath protects the shaft of the microcannula and/or a cover protects the tip of the microcannula during insertion into the eye. Once the microcannula is within the eye the cover is retracted thus exposing the tip. The cover may be slid over the microcannula tip prior to removing the device from the eye in order to minimize tip breakage. A barbed fitting may be attached to the end of the microcannula to aid in attaching the tube that is attached to the syringe.

In an alternate embodiment of the microcannula, the protective tube, needle or larger cannula protects the shaft and the tip of the microcannula and is retracted into the handle to expose the tip. The handle will also protect an otherwise exposed/unprotected portion of the shaft of the microcannula when the protective member is in an extended/outward position over the beveled tip.

If the illumination is incorporated with the microcannula then the illumination component of the infusion cannula may not be necessary. It is also apparent that if an infusion line is required, it may also be incorporated into the microcannula device which may obviate the need for a separate infusion line and/or separate sclerotomy site.

The microcannula may be used to cannulate the retinal vessel manually or alternatively be placed within a holder that aids the surgeon in steadying the device. Another option is to place the microcannula within a micromanipulator such that the microcannula may be manually advanced or automatically advanced into the retinal vessel.

If the retinal vessel chosen for cannulation is in the posterior retina then the microcannula tip is preferably at an approximately 135 degree angle to the shaft such that the tip will be parallel to the lumen of the blood vessel when it is placed through a standard pars plana sclerotomy site. It is apparent that if the blood vessel chosen to be cannulated is in the equatorial or in the peripheral retina than the angle to the shaft would be different so that the microcannula tip will be parallel to the vessel when it is placed through a pars plana sclerotomy site. The location of the sclerotomy site in the eye and its relation to the location of the blood vessel chosen for cannulation affects the tip angle in relation to the shaft. If the microcannula is used to place or remove fluid or material from on top of or underneath the retina than other tip angles are possible.

Fluid may be withdrawn or injected into the retinal vessel or alternatively a catheter, wire, laser fiber, stent, etc. may be advanced through the microcannula for diagnosing, testing or treating an area at or at a distance from the cannulation site. Many other uses of this technology will be apparent to those skilled in the art.

Thus, the present invention provides a device that may safely advance the micropipette into the retinal blood vessel while securely holding it in a stable fashion and allowing rotation in the "X", "Y" and "Z" planes for ease of maneuverability. The apparatus can be easily attached and removed from the operating field, and, is thus portable. The apparatus can be attached by conventional means to the a wrist rest, the operating table, the operating microscope or any other convenient and stable location in the operating room. Additionally, the apparatus is constructed so not to encumber the surgeon's view through the operating microscope, or otherwise interfere with the use of the operating microscope.

Additionally, a self-sealing needle can be provided and can be made of stainless steel, plastic or other biocompatible materials compatible with manufacturing and sterilization requirements. The self-sealing needle tip is at an angle to the shaft such that it can be substantially parallel to the lumen of the blood vessel chosen for perforation. The diameter of the tip and length of the parallel portion of the needle can be dependent on the blood vessel chosen for perforation. The terms perforation and cannulation and the terms blood vessel or structure are used interchangeably throughout this application.

The self-sealing needle comprises an elongated relatively rigid hollow body member having a single angled first end to define a relatively sharp beveled end and a second end, said second end may be attached to a syringe, tubing member, etc. The first body portion can be substantially smaller in size than the second body portion. The outer diameter of the first body portion may be of a smaller diameter than the outer diameter of the second body portion. The first body portion can be permanently disposed at an angular relationship with said second body portion such that the beveled tip will be positioned substantially parallel to the blood vessel to be perforated. The angular relationship can be chosen based on the blood vessel targeted for perforation. The first body member can be sized such that the beveled tip can safely enter the structure. The length of said first body portion and said beveled tip causes a shelved incision in the targeted structure which is self-sealing upon removal of said first body portion and said beveled tip from the perforation site.

Another embodiment of the present invention provides an ocular implant needle. Advances in the diagnosis and pathophysiology of eye diseases have allowed advances in therapy. Delivering therapeutic levels of drugs to the eye has resulted in the development of reservoir and biodegradable ocular implants that are filled with drugs to treat the ocular condition. One such reservoir ocular implant is manufactured by Controlled Delivery Systems of Watertown, Mass.; one such biodegradable ocular implant is manufactured by Oculex Pharmaceuticals of Sunnyvale, Calif. The present invention ocular implant needle is used to lessen the surgical trauma associated with the placement of ocular implants. The ocular implant needle can easily perforate the eye while making a self-sealing perforation site. The needle can also be used for the injection of a drug implant or other device or pharmaceutical agent at a precise location within the eye.

For purposes of the disclosure and claims the terms micropipette, microcannula, cannula and needle are used interchangeably. To the extent that such terms differ in any way in meaning, if any, then the broadest definition for any of the terms is considered to be the definition for all terms for purposes of the instant invention disclosure. It should also be noted that with some uses the size of the device may not be in micron sizes (i.e. drawing blood from a human's arm as opposed to cannulating a human retinal blood vessel).

In accordance with the objects noted above, which will become apparent hereinafter, the instant invention will now be described with particular reference to the accompanying drawings.

BRIEF DESCRIPTION OF THE SEVERAL VIEWS OF THE DRAWINGS

The invention may be better understood by reference to the drawings in which:

FIG. 1 is a front view of a first embodiment for the micropipette (microcannula) of the present invention;

FIG. 2 is a front view of a second embodiment of the micropipette in which an illumination member such as a fiber optic light source is attached to the side of the micropipette to provide illumination during the operation;

FIG. 3 is a front view of a third embodiment of the micropipette wherein the micropipette and fiber optic are enclosed within a protective sheath or tube to minimize breakage when placed into the eye, the protective sheath or tube can also be used for a microcannula without a fiber optic;

FIG. 6 illustrates a view of the micropipette when placed through the sclerotomy site into the eye;

FIG. 7 illustrates the tip of the micropipette overlying and parallel to the retinal blood vessel to be cannulated;

FIG. 8 is a perspective view of the micropipette when placed through the sclerotomy site into the eye;

FIG. 12 illustrates a front view of the seventh embodiment of the microcannula in which the device is encased in a case. The protective sheath may be retracted thus exposing the microcannula tip. An illumination member, such as a fiber optic or other light source may be attached to the microcannula assembly such that the tip of the microcannula or the area surrounding the tip of the microcannula may be illuminated;

FIG. 13 illustrates a front view of the eighth embodiment of the microcannula where the protective sheath may also be substantially sharp;

FIG. 14 is a perspective view of the preferred embodiment for the microcannula, clamp with stabilization post, stabilization arm and illumination positioner attached to a conventional surgeons wrist-rest;

FIGS. 15A–15B illustrate the illumination positioning arm that attaches to the stabilization post and an accessory arm that contains a series of openings in which to place a fiber optic thus directing the angle of the illumination within the eye;

DETAILED DESCRIPTION OF THE INVENTION

Figure 4:
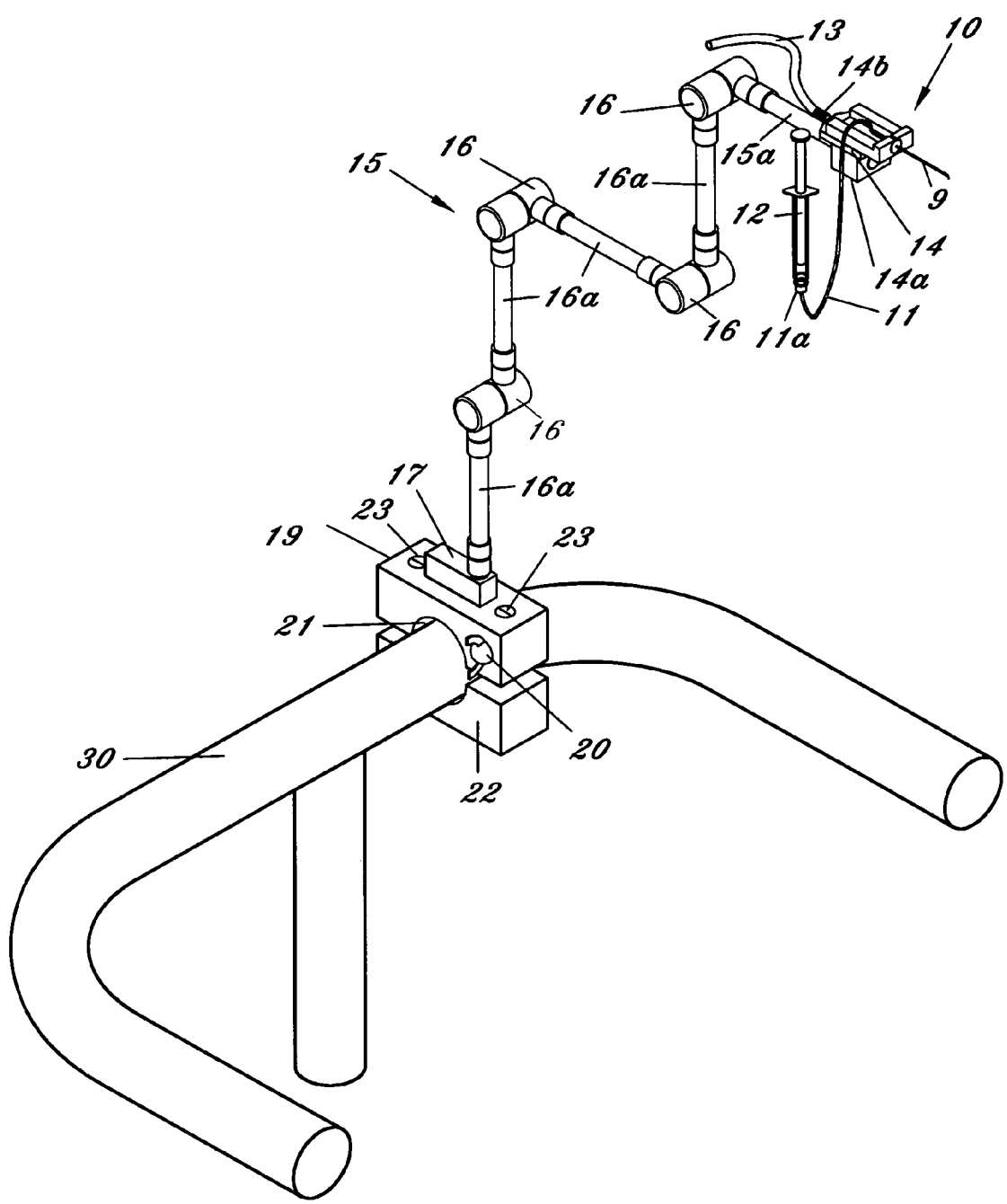
FIG. 4 is a perspective view of the preferred embodiment for the micropipette, micromanipulator, positioner and base of the present invention attached to a conventional wrist rest.

FIG. 1 illustrates a first embodiment for the micropipette/microcannula (1) showing the opening (2) that is preferably connected to a surgical tubing and the tip (3) of the micropipette oriented at an approximately 135 degree angle, although other ranges are possible. Tip (3) can be angled so that it may safely cannulate the retinal vessel when micropipette (1) is placed through a standard retinal surgical sclerotomy site. While glass is suggested for the material because of its ease of fashioning, strength, transparency, etc., other materials may be used. It is essential, however, that the materials maintain substantial strength when fashioned to perform retinal vessel cannulation. A handle (1a) is shown attached to the body member of micropipette (1). Handle (1a) fits securely within a micropipette holder (10) by inserting the end of micropipette (1) associated with handle (1a) and handle (1a) into the front opening of holder (10). Once inserted micropipette (1) is held in place by a setscrew associated with the holder (10).

As seen in FIG. 2, an alternative embodiment of the micropipette/microcannula is illustrated. In this embodiment, a fiber optic (8) is attached to the micropipette body (7) to provide illumination such that an illuminated infusion cannula is not required. If a vitrectomy is not performed then one sclerotomy for the micropipette and fiber optic is all that is necessary. A handle (8a) is provided and fits securely within the holder (10) and is held in place by a set screw within the holder (10), similar to as described for micropipette (1).

FIG. 3 illustrates a further alternative embodiment for the micropipette (4) where a fiber optic for illumination is included (5) and both items are placed within a tube or needle (6). The purpose of the tube or needle is to protect the enclosed instruments such that they may be safely inserted through the sclerotomy site without breakage. Both the fiber optic and the micropipette ends are at the end or protrude from the end of the tube or needle. The micropipette and fiber optic may be advanced through the end of the tube or needle once it has been placed within the eye. A handle (6a) is illustrated that fits securely within the holder (10) and may be firmly held in place by a set screw or locking mechanism within the holder (10), as previously described above. If a vitrectomy is not performed then one sclerotomy for this device is all that is necessary.

FIG. 4 illustrates the micropipette (9) attached to the holder (10). A screw handle (14b), which controls the position of the holder (10), is attached to a flexible tube (13) so the micromanipulator may remotely advance the micropipette. Screw handle (14b) is associated with a micromanipulator (14). Preferably, screw handle (14b) is connected to micromanipulator (14). Holder (10) is attached to the micromanipulator. In one embodiment, the micromanipulator is a miniature translation stage, using dual dowel pin bearings. One such micromanipulator is made by the Newport Corporation located in Irvine, Calif. The Newport micromanipulator has a stage, which has a range of travel of approximately four (4 mm) millimeters, though such measurement is not considered limiting.

Figure 5:
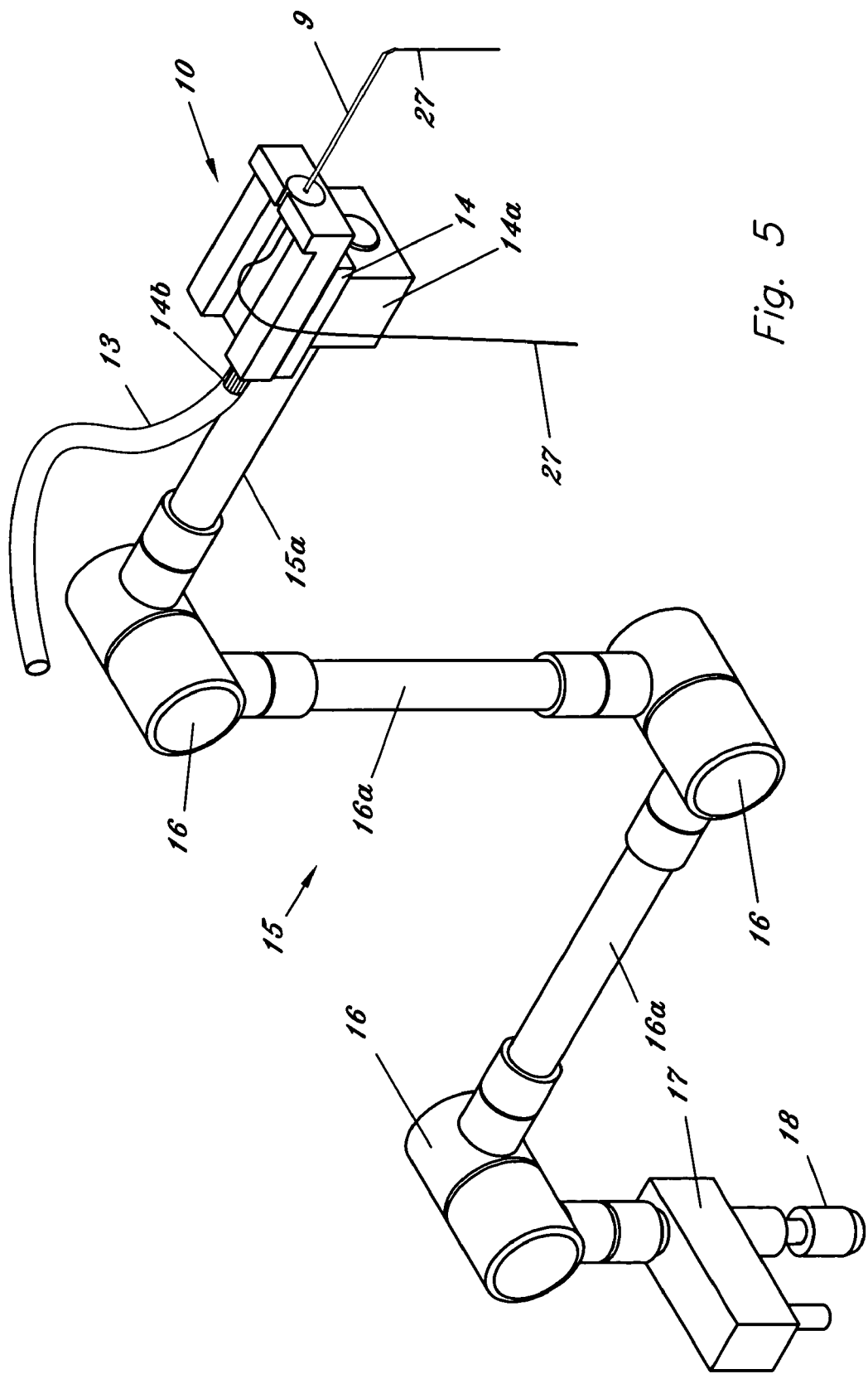
FIG. 5 is another perspective view of the preferred embodiment for the micropipette, micromanipulator, positioner and base of the present invention.

In one embodiment (FIG. 4), the non-tip end of the micropipette is preferably attached to standard surgical tubing (11). The tubing (11) is attached to a connector (11a), which is connected to a syringe (12) that is used to inject medication or withdraw fluid from the retinal blood vessel. In certain situations medication such as t-PA can be injected into the retinal vessel. Alternatively, a dye can be injected into the retinal vessel for diagnosing purposes. Alternatively, a catheter, wire or stent (27) may be advanced through the microcannula for diagnosing, testing or treatment of an area located at a distance from the insertion site (FIG. 5).

A foot pedal or other switch may also be provided to control (i.e. electrically, pneumatically, mechanically, etc.) the micromanipulator and injector or withdrawing device so it may be activated by the surgeon. These alternative embodiments are considered within the scope of the invention.

The micromanipulator (14) is attached to a base (14a) which is attached to a positioner (15) that is freely mobile in the "X", "Y" and "Z" planes due to the multiplicity of joints (16), connected by elongated members (15a and 16a). The positioner may also be electrically controlled by servomotors and activated by the surgeon with a foot pedal or other switch. Such alternatives are also considered within the scope of the invention. Positioner (15) is not limited to any specific amount of elongated members.

The positioner can be attached to a base (17). In one embodiment, an attachment post (18) fits into a hole within another base (19). Preferably, set screws or wing nuts (20), are provided, on either side of the base which is used to secure the post to the base. In order to make the base secure, base (19) attaches to another base (22) by two screws (23). Base (19) fits above the standard ophthalmic surgical wrist rest (30) which is oriented perpendicular to bases (19) and (22). The wrist rest fits within the hole (21) that exists between bases (19) and (22). Base portion (22) completes the base and is located underneath the wrist rest. Alternatively, the positioner may be attached directly to the wrist rest or connected to the operating microscope or operating table. Additionally, the bases can be sized to fit other objects in the operating room. Changes in modifications within the spirit and scope of the invention will be apparent to those skilled in the art. Such modifications and changes are intended to be covered by the claims herein.

As seen in FIGS. 6 through 8, a sclerotomy can be made at the standard distance from the limbus and an illuminated infusion cannula can be placed through the sclera at this point. A pars plana vitrectomy may or may not be necessary with further experience. Another or second sclerotomy can be made at the standard distance from the limbus such that the micropipette/microcannula is substantially parallel to the retinal blood vessel chosen to be cannulated. The micropipette is then placed through the sclerotomy overlying the selected retinal blood vessel. The intraocular pressure can be lowered to approximately 5 mm of Mercury to allow dilation of the vessel. Once the blood vessel is perforated, it may be advantageous to raise the intraocular pressure to minimize bleeding. The retinal blood vessel may be cannulated manually or the micromanipulator used to advance the micropipette into the retinal blood vessel.

Figure 9A:
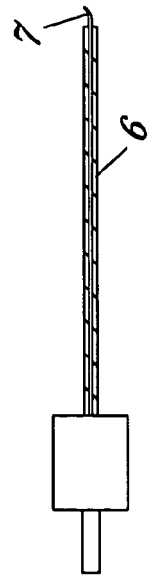
FIGS. 9A–9B illustrate a front view of the fourth embodiment of the microcannula in which the shaft of the microcannula is enclosed by a protective sheath.
Figure 9B:
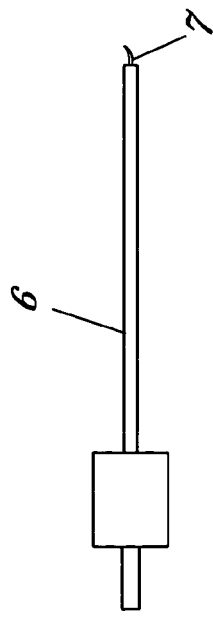

FIGS. 9A and 9B illustrate a front view of the fourth embodiment of the microcannula in which the shaft (7) of the microcannula is enclosed by a protective sheath (6).

Figure 10A:
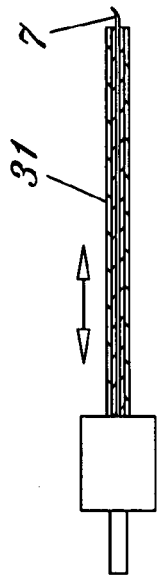
FIGS. 10A–10B illustrate a front view of the fifth embodiment of the microcannula in which the shaft of the microcannula is enclosed within a protective sheath with a cover that retracts and exposes the tip of the microcannula.
Figure 10B:
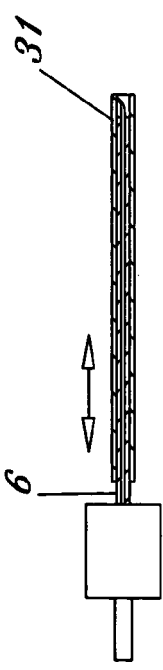

FIGS. 10A and 10B illustrate a fifth embodiment for the microcannula showing the microcannula (7) within a protective sheath (6) that protects the shaft of the microcannula and protective cover (31) that protects the tip of the microcannula (FIG. 10A). The protective sheath and cover may be made of metal, plastic, or other materials that protects the shaft and tip of the microcannula. As seen in FIG. 10B, the cover may be retracted once the microcannula is within the eye and is replaced or extended outwards once the procedure is complete and the microcannula is ready for removal from the eye, such that tip breakage is minimized.

Figure 11A:
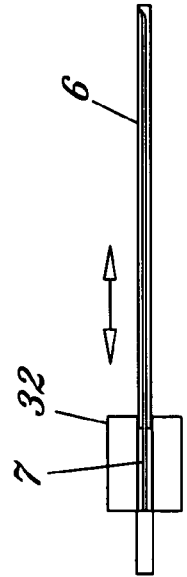
FIG. 11 illustrates a front view of the sixth embodiment of the microcannula in which the protective sheath may be retracted thus exposing the microcannula tip.
Figure 11B:
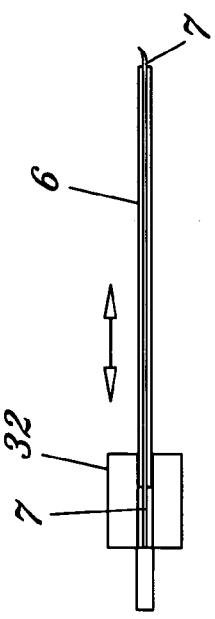

FIGS. 11A and 11B illustrate a front view of the sixth embodiment of the microcannula in which the protective sheath (6) may be retracted into the handle (32) thus exposing the microcannula tip (FIG. 11A). Handle (32) also protects an otherwise exposed/unprotected portion of the shaft (7) of the microcannula when the protective member is in an extended/outward position over the beveled tip (FIG. 11B). The handle attached to the various microcannulas of the invention, including but not limited to handle (32) can be constructed from various materials such as nylon, plastic, delfin, etc.

FIG. 12 illustrates a seventh embodiment for the microcannula, wherein a portion of the shaft of the microcannula is encased in a hard case (33) which may be made from plastic, metal, or another robust material. An illumination member, such as a fiber optic (34) traditionally used in retinal surgery, or another illumination member or light source, may be attached to the case and secured in place by a gasket assembly (35). The type of light source and method of attachment will determine the size and degree of illumination provided. Alternatively, the light member may be attached within or outside the protective cover. The side port (36) is in communication with a device or tubing that is connected to a syringe or other device that will allow the injection or egress of fluid or other material through the microcannula.

FIG. 13 illustrates an alternate embodiment for the microcannula assembly where the tip (33) of the sheath (6) surrounding the microcannula may be sharp enough to perforate the sclera. This embodiment obviates the need for the traditional knife or MVR blade that is generally used by the surgeon to make a hole in the sclera, or sclerotomy, through which the surgeon places instruments into the eye. Once the device is inside the eye, the sheath (6) is retracted exposing the tip of the microcannula and the procedure is performed.

FIG. 14 illustrates a microcannula (i.e. any of the microcannulas disclosed herein) which can be attached to a stabilization arm (42) by a holder (43) and set screw assembly (44) or similar device. The holder (43) includes a clamp mechanism that allows for different sizes of microcannulas to be retained. The stabilization arm (42) is preferably maneuverable in the x-y-z positions and may be connected by another set screw assembly (35) with clamp mechanism (36) or similar device to a stabilization post (38) which can be attached to a clamp (39) that can be attached to a standard surgical wrist-rest (30) or other object. The tension within the stabilization arm is controlled by a tension control assembly (45). The tension along the stabilization arm controls the flexibility of the arm. The stabilization arm may be loosely tightened such that it is sufficiently flexible along its length and allows the microcannula to be easily placed into the eye. Prior to the cannulation of the retinal blood vessel, the tightening of the stabilization arm by the tension control assembly is performed such that the microcannula is steady within the eye, but where small movements are still possible with mild force by the surgeon, if desired. This allows the surgeon to place the microcannula within the blood vessel and allows it to maintain its position within the blood vessel during an infusion of medication, withdrawal of a sample, placement of an instrument, etc. The force required by the surgeon against the stabilization arm dampens any unintended movement by the surgeon such as tremor which may occur during the procedure.

FIGS. 15A and 15B illustrate the illumination positioning arm (37). As seen in FIG. 14, illumination positioning arm (37) attaches to the stabilization post (38) through circular member (39). The arm is held in place by a set screw (39a). One or more, and preferably a series of, openings (40) are placed within an accessory arm (41) that is secured to the illumination positioning arm by a set screw (41a). By setting the angle of the illumination positioning arm in relation to the patient's head, the location of the accessory arm, and the opening in which the fiber optic (49) is placed, the desired location/intensity of illumination within the eye is achieved.

The stabilization arm, stabilization post and illumination positioning arm and accessory arm are preferably made from an easily sterilizable material, such as stainless steel or rubber, though other materials may be used and are considered within the scope of the invention.

In all embodiments, where the micropipette/microcannula is used for cannulating a retinal blood vessel it can be preferably designed to fit a eighteen (18) through twenty (20) gauge sclerotomy site. However, such is not limiting and other gauge sclerotomy sites can be chosen, and the micropipette designed accordingly, and are considered within the scope of the invention.

Though not to be considered limiting, the dimension ranges for the micropipette/microcannula for all embodiments when used for cannulating retinal blood vessels, can preferably consist of the following:

(a) first body portion associated with beveled tip end having a length range of between approximately 500 microns to approximately 1000 microns;

(b) tip end beveled at a range of between approximately twenty (20°) degrees to approximately thirty (30°) degrees;

(c) second body portion associated with handle having a length range of between approximately 60 millimeters to approximately 100 millimeters;

(d) beveled tip end having an outer diameter range of between approximately 50 microns to approximately 100 microns and an inner diameter range of between approximately 40 microns to approximately 70 microns; and (e) angle between first body portion and second body portion having a range of between approximately 100° degrees to approximately 180° degrees, depending on area in which it is used for.

Figure 16:
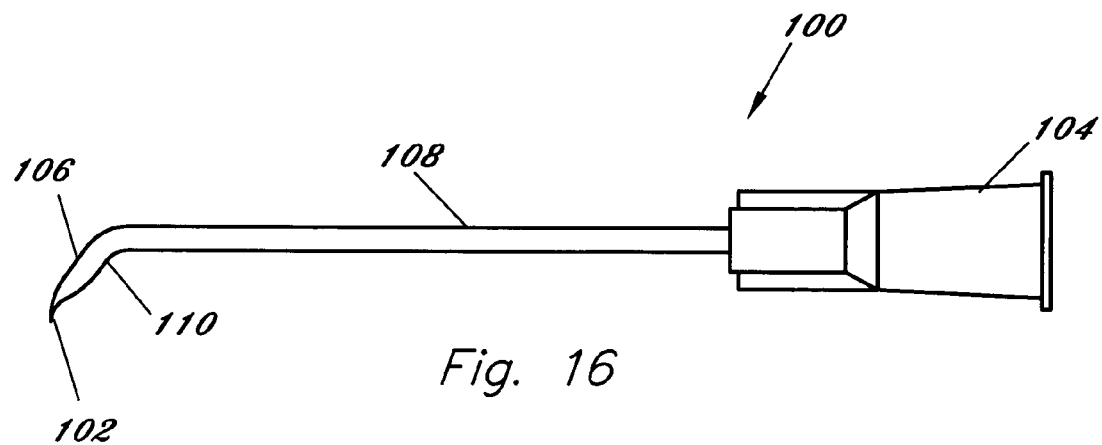
FIG. 16 illustrates a self sealing needle embodiment of the present invention.

As seen in FIG. 16 a self-sealing needle 100 is provided and can be made of stainless steel, plastic or other biocompatible materials compatible with manufacturing and sterilization requirements. A self-sealing needle tip 102 can be provided at an angle to the shaft such that when used properly it can be substantially parallel to the lumen of the blood vessel chosen for perforation. The diameter of tip 102 and length of the parallel portion of the needle can be dependent on the blood vessel chosen for perforation. The terms perforation and cannulation and the terms blood vessel or structure are used interchangeably throughout this application.

The self-sealing needle comprises an elongated relatively rigid hollow body member having a single angled first end to define a relatively sharp beveled end and a second end, said second end may be attached to a syringe, tubing member, etc., directly or through a conventional attachment mechanism 104. A first body portion 106 can be substantially smaller in size than a second body portion 108. The outer diameter of first body portion 106 may be of a smaller diameter than the outer diameter of second body portion 108. First body portion 106 can be permanently disposed at an angular relationship 110 with second body portion 108 such that beveled tip 102 can be positioned substantially parallel to the blood vessel to be perforated when used properly. Angular relationship 100 can be chosen based on the blood vessel targeted for perforation. First body portion 106 can be sized such that beveled tip 102 can safely enter the structure. The length of first body portion 106 and beveled tip 102 causes a shelved incision in the targeted structure which is self-sealing upon removal of first body portion 106 and beveled tip 102 from the perforation site.

As an example only, a self-sealing needle 100 that could be used to perforate the brachial vein in a normal, healthy 40-year-old male might consist of a 21 gauge tip 102 that can be beveled at an angle of approximately 20 degrees. The length of first body portion 106 can be approximately 4 mm and angular relationship 100 between the first and second body portions can be approximately 135 degrees.

Figure 17:
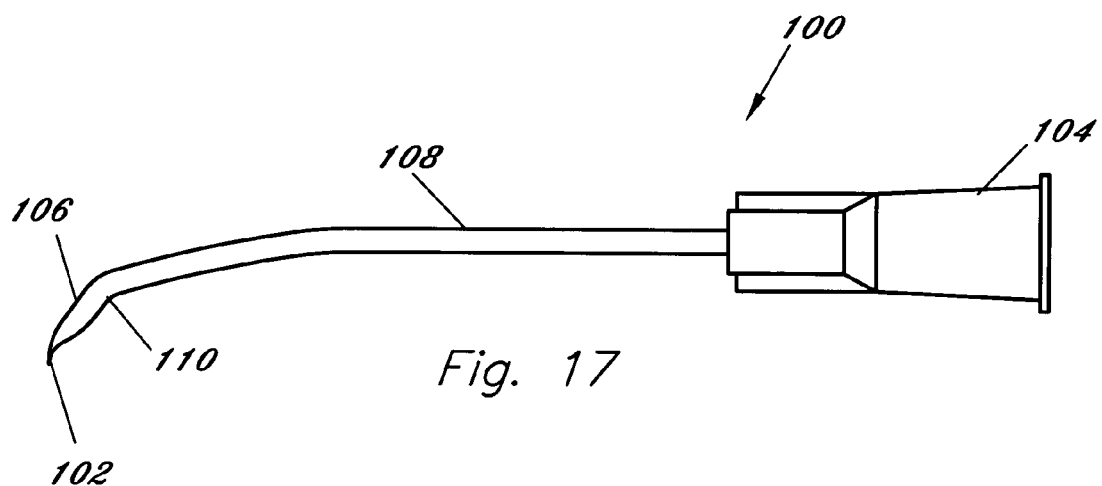
FIG. 17 illustrates the self sealing needle of FIG. 16 having a curved portion.

Additionally, second body portion 108 of self-sealing needle 100 can be curved (See FIG. 17). Another variation is where a portion of the shaft is curved. An additional variation is where the shaft has multiple different curves. You can use this device is situations where a needle or cannula is required, to perforate or cannulate a blood vessel or other structure.

The length of second body portion 108 is appropriate for the structure chosen for perforation. A deeper structure may require a longer second body portion than a more superficial structure. Second body portion 108 may be straight, curved with the same or different curves along its length, or only a portion of second body portion 108 may be curved to facilitate perforation of the chosen structure. Though not limiting in range, the curve or curves of second body portion 108 may be between approximately 0 degrees to approximately 50 degrees.

Figure 18:
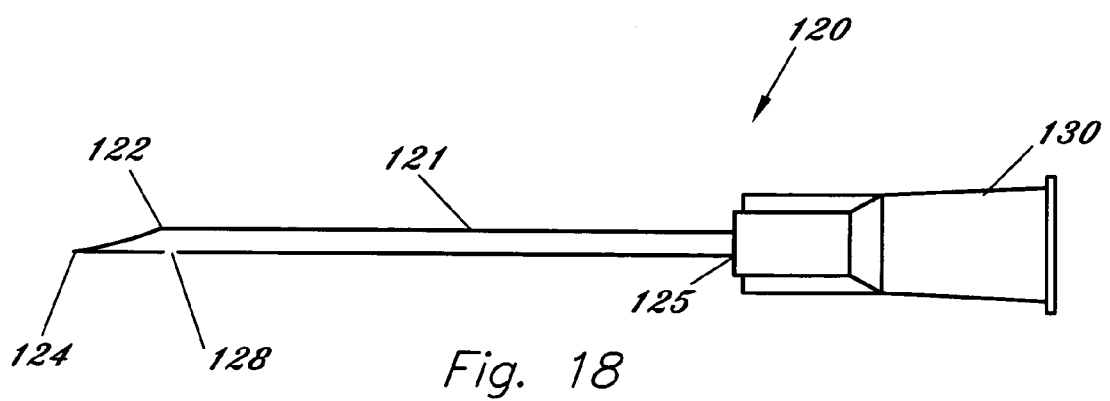
FIG. 18 illustrates a substantially straight ocular implant needle embodiment of the present invention having a flange and hole.

FIG. 18 illustrates an ocular implant needle embodiment of the present invention which is generally referenced as needle 120. In order to facilitate the placement into the eye of a drug implant, ocular prosthesis, sensor or other device or pharmaceutical agent a flange or other marking device (e.g. protrusion, bump depth mark, etc. all collectively referred to as "marking device") 122 may be placed at a desired location from the extreme tip 124 of needle 120 along its length. The position of flange or marking device 122 depends on the length of the object or substance to be inserted in the eye and the properties of the item to remain in the desired location and not migrate.

Straight needles approximately 25 gauge and smaller will generally make self-sealing perforation sites when placed through the sclera of the eye. However, other gauge needles could be used as an ocular implant needle if provided in a curved or bent configuration, such as, but not limited to, the needles illustrated in FIGS. 16 and 17 herein. Preferably, needle 120 can fall within this gauge range to permit a self-sealing perforation site to be achieved. Though no limitation to the invention is implied by the following example, an ocular implant that is 2 mm in length and sized to fit within a 30 gauge needle that is to be placed through and remain at the pars plana of the eye might have a flange 122 that prevents needle 120 from being further introduced deeper into the eye at end 124 of the bevel of needle 120, approximately 1 mm from tip 124 of needle 120. A hole or holes 128 in the shaft 121 of needle 120 at some distance above or from flange 122 may be provided depending on the length, the stability properties, the location of placement and other properties of the item to be injected into the eye. Needle 120 preferably comprises a relatively rigid hollow body member 121, which can be elongated or substantially straight, having a relatively sharp beveled first end 124 and a second end 125. Second end 125 may be attached to a syringe, tubing member, etc., directly or through conventional attachment mechanism 130.

As the surgeon slowly injects, the injectable item passes hole 128 in shaft 121 thus releasing the pressure within shaft 121 of needle 120 and slowing the rate of injection as the item nears needle tip 124. The release of pressure within needle 120, the visualization of escaping fluid, gas or the displacement of the surrounding fluid, hemorrhage or other objects near hole or holes 128 in needle shaft 121 alerts the surgeon to be more careful as the injectable item is reaching end 124 of needle 120 and its desired location. Once the injection is complete, the surgeon withdraws needle 120 from the eye in standard fashion.

In an alternative embodiment for needle 120, a portion or all of shaft 121 can be transparent and provided with or without one or more holes 128. Any percentage amount of transparent portion is considered within the scope of the invention. As being at least partially transparent, any device or liquid traveling through shaft 121 can be seen by the surgeon who can determine how much pressure to exert based on the location of the device or liquid within shaft 121. Preferably, flange 122 or other marking device can be provided with this alternative needle 120 embodiment, and the other alternative needle 120 embodiments discussed below.

In an another needle 120 embodiment, shaft 121 is either opaque or transparent. One or more holes 128 is either covered with a membrane like material or plastic or like material. Where a membrane like material is provided, if too much pressure is applied by the surgeon, the membrane is designed to burst or pop, similar to a balloon popping. Where a plastic or other transparent like material is provided, the item can be seen traveling through shaft 121 at the location of one or more holes 128.

In a further needle 120 embodiment, at least one slit in a side area of shaft 121 can be provided for monitoring the travel of the item within shaft 121. Similar to the preceding paragraph, a membrane like material or plastic/transparent like material can be provided to cover the at least one slits.

The membrane like material or plastic/transparent like material can be disposed over or within holes 128 or the slits by any conventional attachment method. It is also within the scope of the invention that only a portion of the membrane like material or plastic or like material is transparent. For example, though not considered limiting, the portion of the membrane, plastic or like materials could be transparent at the portion which is aligned with holes 128 or slits, to permit visibility within shaft 121, with other portions of the material not required to be transparent.

It is also within the scope of the invention to provide a needle 120 having any combination of features chosen from all of the features discussed above for the needle 120 embodiments.

Needle 120 may also be used to place implants, prosthesis, drugs, devices, etc. elsewhere in the eye, i.e. the choroid, the subretinal space, etc. in a desired area within the eye, i.e. anteriorly, posteriorly, etc. The injected implant or device may contain barbs or other aids to assist in the implantation and help prevent the migration of the device. Needle 120 can be constructed from materials or combination of materials similar to those described above for the embodiments illustrated in FIGS. 16 and 17.

The angle of entry for needle 120 into the eye and the location of the flange or other marking device 122 may allow the placement of the injectable device or substance at various locations within the eye. If a mm scale along the side of shaft 121 of needle 120 is used as a marking device then the same needle 120 may be used to place the item at different locations within the eye. As an example only and not considered limiting, perforating the sclera at the 4 o'clock position and angling needle 120 toward the opposite pars plana may allow the placement of the device or substance in the pars plana at the 8 o'clock position. In this situation the surgeon would "feel" needle 120 touching the opposite internal side of the eye and would then inject. It is also apparent that the plunger on the syringe may be connected to a rod or other device that physically pushes the device to be injected out of the end of needle 120.

Similar to earlier embodiments of the invention discussed above, shaft 121 can be provided in a bent or angled configuration to allow needle 120 to create a shelved incision at its point of entry in the eye.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A needle comprising:
   a relatively rigid hollow body member having a single angled first end to define a relatively sharp beveled tip, a second end connected to and in internal communication with a delivery device, an internal passageway and an externally disposed aperture, and
   a marking device disposed on said body member;
   wherein said aperture disposed between said marking device and said second end and is accessible to the user while in use.

2. The needle of claim 1 wherein the body member is one-piece and substantially straight.

3. The needle of claim 2 wherein the size of said body member along with said beveled tip causing an incision at the perforation site which is self sealing upon removal of said body member including said beveled tip from the perforation site.

4. The needle of claim 1 wherein said marking device is a flange.

5. The needle of claim 1 wherein said beveled tip is non-movable and said body member being sized such that the beveled tip can safely enter into the perforation site.

6. The needle of claim 1 wherein said body member is constructed from a biocompatible material.

7. The needle of claim 1 wherein said biocompatible material is stainless steel.

8. The needle of claim 1 wherein said biocompatible material is plastic.

9. The needle of claim 1 wherein said marking device is positioned on said body member approximate to said first end of said body member.

10. The needle of claim 1 wherein at least a portion of said body member is transparent.

11. An ocular implant needle comprising:
a relatively rigid hollow body member having a single angled open first end to define a relatively sharp beveled tip and a second end connected to and in internal communication with a device for delivering an ocular implant, said body member defining at least one externally disposed aperture therein; and
a flange disposed on said body member approximate to said first end of said body member; said at least one externally disposed aperture disposed between said flange and said second end of said body member;
wherein said aperture is accessible to the user while in use and is sized to prevent the ocular implant traveling through said body member from escaping through said aperture.

12. The ocular implant needle of claim 11 wherein the body member is one-piece and substantially straight.

13. The ocular implant needle of claim 11 wherein the size of said body member along with said beveled tip causing an incision at the perforation site which is self sealing upon removal of said body member including said beveled tip from the perforation site.

14. The ocular implant needle of claim 11 wherein said beveled tip is non-movable and said body member being sized such that the beveled tip can safely enter into the perforation site.

15. An ocular implant needle comprising:
an elongated, relatively rigid hollow one-piece body member having a single angled open first end to define a relatively sharp non-movable beveled tip and a second open end connected to and in internal communication with a device for delivering an ocular implant, said body member defining an internal passageway extending from said first end to said second for receipt of the ocular implant and also defining at least one externally disposed aperture therein, said externally disposed aperture providing atmospheric communication for at least a portion of said internal passageway during use of said body member as a needle; and
a flange disposed on said body member approximate to said first end of said body member; said at least one externally disposed aperture disposed between said flange and said second end of said body member;
wherein said aperture is accessible to the user while in use and is sized to prevent the ocular implant received within said body member from escaping through said aperture.

16. The ocular implant needle of claim 15 wherein the size of said body member along with said beveled tip causing an incision at the perforation site which is self sealing upon removal of said body member including said beveled tip from the perforation site.

17. The ocular implant needle of claim 15 wherein said body member being sized such that the beveled tip can safely enter into the perforation site.

* * * * *

UNITED STATES PATENT AND TRADEMARK OFFICE
CERTIFICATE OF CORRECTION

PATENT NO.       : 6,936,053 B1                                    Page 1 of 1
APPLICATION NO.  : 10/421425
DATED            : August 30, 2005
INVENTOR(S)      : Jeffrey N. Weiss It is certified that error appears in the above-identified patent and that said Letters Patent is hereby corrected as shown below:

Drawings:

Substitute Fig. 18, with corrected Fig. 18 below:

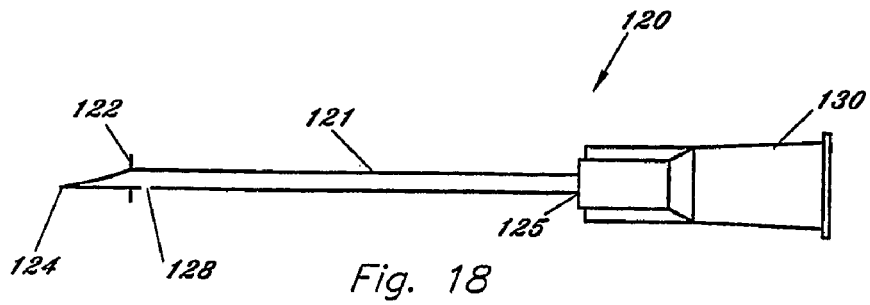

Fig. 18

Signed and Sealed this

Second Day of October, 2007

JON W. DUDAS
*Director of the United States Patent and Trademark Office*